United States Patent [19]

Lottick

[11] Patent Number: 4,686,985
[45] Date of Patent: Aug. 18, 1987

[54] ANAL DILATOR AND OCCLUDER

[76] Inventor: Edward A. Lottick, 789 Wyoming Ave., Kingston, Pa. 18704

[21] Appl. No.: 853,680

[22] Filed: Apr. 24, 1986

Related U.S. Application Data

[63] Continuation-in-part of Ser. No. 734,294, May 15, 1985.

[51] Int. Cl.$^4$ ............................................. A61M 29/02
[52] U.S. Cl. ................................................... 128/344
[58] Field of Search ............... 128/344, 325, DIG. 25, 128/327, DIG. 20, 346; 604/99, 96, 101, 41, 278, 54

[56] References Cited

U.S. PATENT DOCUMENTS

| | | | |
|---|---|---|---|
| 397,060 | 1/1889 | Knapp | 604/96 |
| 2,499,045 | 2/1950 | Walker et al. | 128/344 X |
| 2,693,191 | 11/1954 | Raiche | 604/101 |
| 2,813,531 | 11/1957 | Lee | 604/103 |
| 3,154,077 | 10/1964 | Cannon | 128/325 |
| 3,459,175 | 8/1969 | Miller | 128/654 |
| 3,509,884 | 5/1970 | Bell | 604/101 |
| 3,625,793 | 12/1971 | Sheridan et al. | 604/101 X |
| 3,707,151 | 12/1972 | Jackson | 128/207.15 |
| 3,848,602 | 11/1974 | Gutmick | 128/344 |
| 3,889,676 | 6/1975 | Greene | 604/101 |
| 4,019,515 | 4/1977 | Kornblum et al. | 604/101 |
| 4,022,216 | 5/1977 | Stevens | 604/101 |
| 4,248,234 | 2/1981 | Assenza et al. | 128/344 X |
| 4,423,725 | 1/1984 | Baran et al. | 128/207.15 |
| 4,555,242 | 11/1985 | Saudagar | 128/344 X |

Primary Examiner—Michael H. Thaler
Attorney, Agent, or Firm—Michael F. Petock

[57] ABSTRACT

An inflatable device is disclosed which is comprised of three chambers which are adapted to be inserted partially into the rectum and inflated. The first chamber would be positioned within the rectum, the second within the anal sphincter muscles and the third outside of the body between the buttocks. When used for dilation, the first and third chambers are utilized primarily for positioning and maintaining the position. The second chamber is selectively inflated to perform the dilation function. When utilized as an obturator, to alleviate fecal incontinence, the first and third chambers are utilized to some degree for positioning and maintaining of position, and the first chamber is also utilized, to some degree along with the second chamber as a means of obturating or maintaining fecal continence.

3 Claims, 16 Drawing Figures

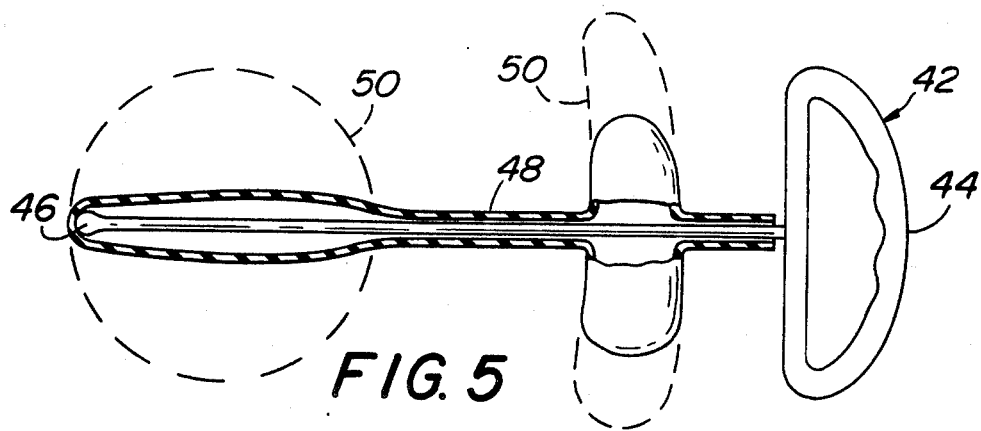
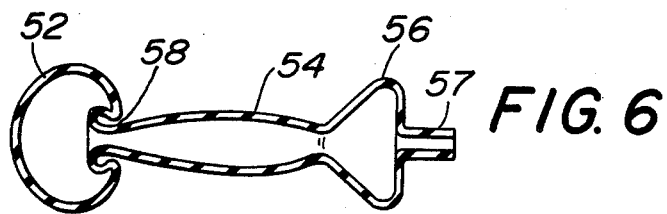
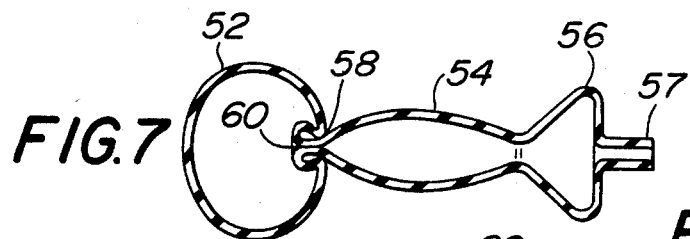
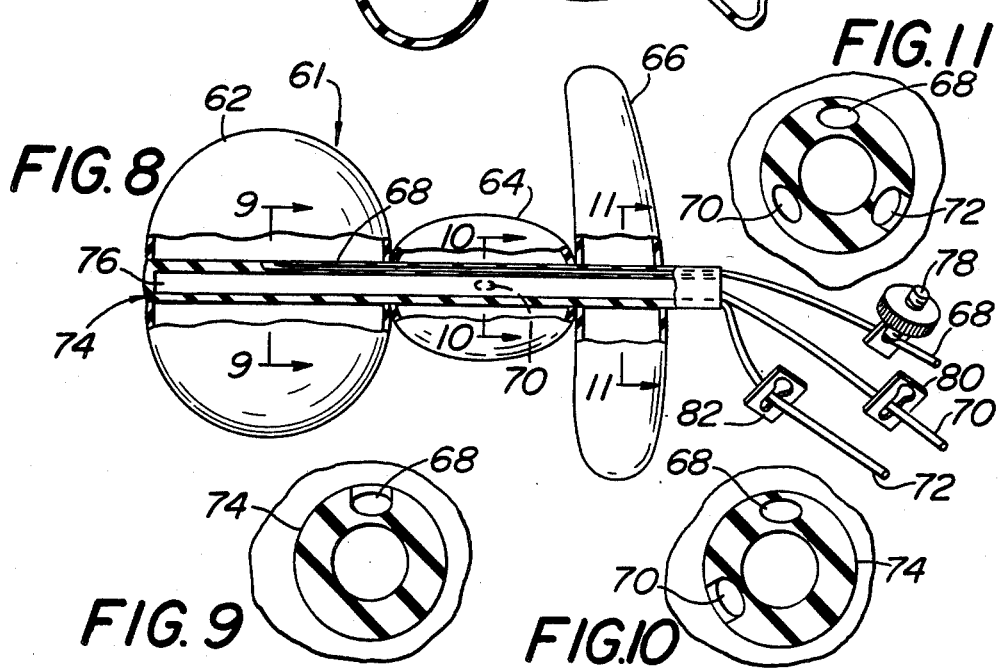

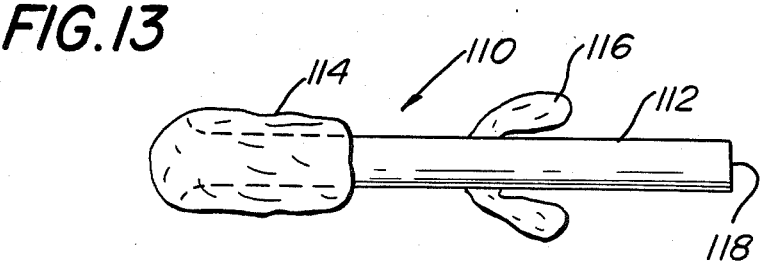
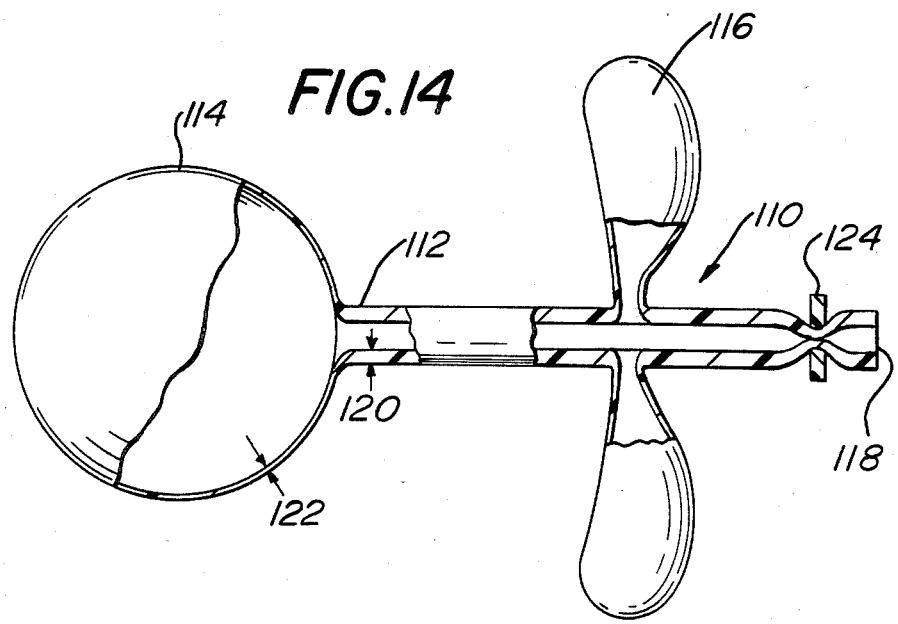
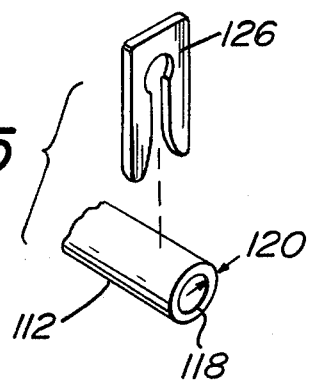
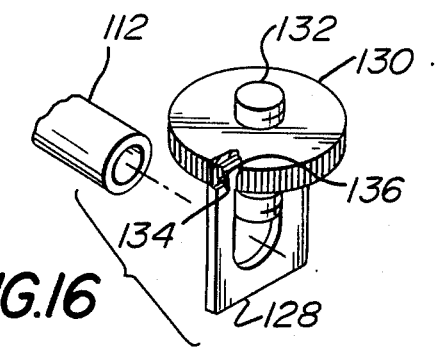

ANAL DILATOR AND OCCLUDER

CROSS REFERENCE TO RELATED APPLICATIONS

This application is a continuation-in-part application of application Ser. No. 734,294, filed May 15, 1985 by Edward A. Lottick, M.D., entitled ANAL DILATOR AND OCCLUDER, now abandoned.

BACKGROUND OF THE INVENTION

The present invention relates to an anal dilator and occluder which may be utilized for dilating the anus for the purpose of medical treatment or serving as an occlusion device for patients suffering from fecal incontinence. More particularly, the present invention relates to a pneumatically operated apparatus adapted for such uses.

A significant number of patients have relative degrees of rectal stricture. A "rectal" stricture is a rather painful and annoying tightening of the lower end of the bowel, usually due to scar formation and usually at the base of the anus. Some rectal strictures are so severe that only a limited opening may be achieved. In such a case, it is difficult for the patient to excrete feces. A person with an anal stricture must essentially squeeze out his/her stool through a small aperture. This causes a significant degree of straining, and it is necessary for such people to frequently take stool softeners in order to keep out of trouble.

Often, the rectal or anal stricture may result from scarring following a hemorrhoidectomy.

Such rectal or anal stricture may be treated by considerable use of stool softeners, surgery or dilation of the anus. The surgical approach is usually regarded as a last resort since patients typically become incontinent following an anal sphincterotomy. This is so since the scar tissue (connective tissue) fibers are usually intertwined with the muscle fibers of the anal sphincter muscles and the anal sphincter muscles must be severed during the surgery. This results in a lax external sphincter and loss of control. It is believed that about fifty percent of the patients which become incontinent due to this surgery eventually regain continence after some period of time, but even in this fifty percent, the time period of incontinence is measured in months.

The more desirabled approach to anal or rectal strictures is that of dilation. The present invention provides a method and apparatus whereby such dilation may be done in a continuous, rather than a stepwise manner. Various types of fixed anal dialators are known in the prior art, such as those commercially available by the medical supply houses. However, none of these are anything like the pneumatic apparatus of the present invention. The present invention may be utilized to effectively treat anal strictures in a safe, efficient and more comfortable manner due to its pneumatic operation which provides a continuous range of dilation.

Another significant medical problem which may be treated by use of the anal dilator of the present invention is that of hemorrhoids. The use of anal dilation in the treatment of hemorrhoids has been recognized in the medical literature, for example see the *Journal of Royal Society of Medicine*, Volume 76, October 1983, pages 901 to 902. The pneumatic anal dilator of the present invention may be utilized in the treatment of hemorrhoids, which is a widespread medical problem. According to physiological concepts, when the pressure increases in the hemorrhoidal plexus of veins, the hemorrhoidal veins surrounding the anus tend to bulge. This sets up irritation and the irritaion causes the hemorrhoidal veins to bulge further. Although increased pressure in the portal vein due to cirrhosis may be a cause of hemorrhoids, due to the widespread occurrence of hemorrhoids, this is probably not the cause of hemorroids in the vast majority of people, but the hemorrhoids are caused in the majority by a cycle of irritation and swelling. Gentle counterpressure from a pneumatic anal dilator in accordance with the present invention may help significantly by interrupting the swelling and bulging parts of the cycle. The pneumatic anal dilator of the present invention would produce a counterpressure where the hemorrhoids would tend to prolapse.

Another significant and widespread problem which may be treated by the apparatus of the present invention is that of fecal incontinence. As the population ages, there tends to be an enlarging number of senile patients, and the severely senile patients are almost always incontinent of both urine and feces. It has been known in the prior art to control urinary incontinence by the use of an indwelling Foley catheter. However, the significant problem, and probably the more significant problem from both an aesthetic point of view and a nosocomial infection rate point of view, is that of the fecal incontinence. Fecally incontinent patients, both in nursing homes and hospitals, place a significant burden on the nursing staff with respect to the cleaning up of feces from fecally incontinent patients. In some nursing homes the number of fecally incontinent patients has been estimated to be between twenty-five to fifty percent of the patients. The burden from the point of view of nursing time, expense, and aesthetics is enormous when viewed in terms of the cleaning up of the feces which typically gets all over the patient, the pajamas, the bed clothes, the floor and sometimes even the wall. This is an aesthetics problem for both the patient and the nursing staff.

However, probably more importantly, fecal incontinence causes a serious problem with respect to the nosocomial infection rate. Even with the best of precautions, where twenty-five to fifty percent of the nursing home patients are fecally incontinent, the rooms have extensive coverage of coliform bacteria. It has been estimated that one of the most common causes of death in the geriatric population in nursing homes is that of infectious disease, often by gram-negative septicemia, greatly exceeding the rate at which patients succumb to vascular occlusive, embolic or neoplastic disease combined. The fecal incontinence problem also has a sever adverse effect in patients, particularly the senile, who may have sacral decubiti, with the feces contaminating these open sores.

The present invention is of significant value for anal dilation, treatment of hemorrhoids and fecal incontinence.

SUMMARY OF THE INVENTION

In accordance with the present invention, an apparatus is provided for partial insertion into the anus of a living being which comprises an inflatable element which in turn comprises a plurality of chambers when inflated. The plurality of chambers, when the element is inserted into the anus and inflated, includes a first chamber of substantially spherical shape to be positioned within the rectum. A second chamber is of a substantially elongated shape which is positioned within the anal sphincter muscles and a third chamber comprises a transverse elongated shaped chamber, adapted when inflated, to lie outside of the body between the buttocks. Valve means are provided for retaining or releasing the inflating fluid in the inflatable element.

In another embodiment of the present invention, the second chamber which is adapted to be positioned within the anal sphincter muscles may not be inflatable, or a tubular element may be utilized in lieu thereof.

The apparatus of the present invention may be inserted into the rectum by use of a blunt trochar. Various types of valve means may be utilized including pinch-off valves and conventional air valves. Any suitable means may be utilized to inflate the chambers, including a compression bulb, such as a sphygmomanometer bulb.

In another embodiment of the present invention, a separate passageway is provided for inflation and deflation of each chamber. The passageway may be provided in various means, including the positioning of such passageways within an annular structure wherein the trochar may be inserted through the center of the annular structure with the separate passageways being mounted within the walls of the annular structure.

In another embodiment of the present invention, the use of an insertion trochar may be eliminated by the use of a relatively rigid stem which may preferably be comprised of a substantially thicker material than the walls of the inflatable chambers.

Throughout, reference will be made to persons who are patients, and the use of the apparatus of the present invention in the rectum or the anus of such persons or patients, however, it is understood that the present invention is not so limited, and may be utilized in the connection with the treatment of any species of animal having a similar structure, such as in the veterinary field of medicine.

BRIEF DESCRIPTION OF THE DRAWINGS

For the purpose of illustrating the invention, there are shown in the drawings forms which are presently preferred, it being understood, however, that this invention is not limited to the precise arrangements and instrumentalities shown.

FIG. 5 is a view of the uninflated apparatus of FIGS. 1 and 2, partially in cross-section and showing an insertion trochar.

FIG. 6 is a cross-sectional view of an alternate embodiment of the present invention.

FIG. 7 is a cross-sectional view of the alternative embodiment shown in FIG. 6 with a greater degree of inflation.

FIG. 8 is an elevation view partially in cross-section, showing an alternate embodiment of the present invention, having three separately inflatable chambers, each having its own passageway.

FIG. 9 is a cross-sectional view taken along line 9—9 of FIG. 8.

FIG. 10 is a cross-sectional view taken along line 10—10 of FIG. 8.

FIG. 11 is a cross-sectional view taken along line 11—11 of FIG. 8.

FIG. 13 is an elevation view of another embodiment of the present invention in its deflated condition.

FIG. 14 is an elevation view partially in cross section of the embodiment of FIG. 13 in its inflated condition.

FIG. 15 is a view in perspective of a clip which may be utilized as shown in FIG. 14 as a valve means.

FIG. 16 is a view in perspective of a clamp structure which may be utilized as a valve means in accordance with the various embodiments of the present invention.

DETAILED DESCRIPTION OF THE PREFERRED EMBODIMENTS

Figure 1:
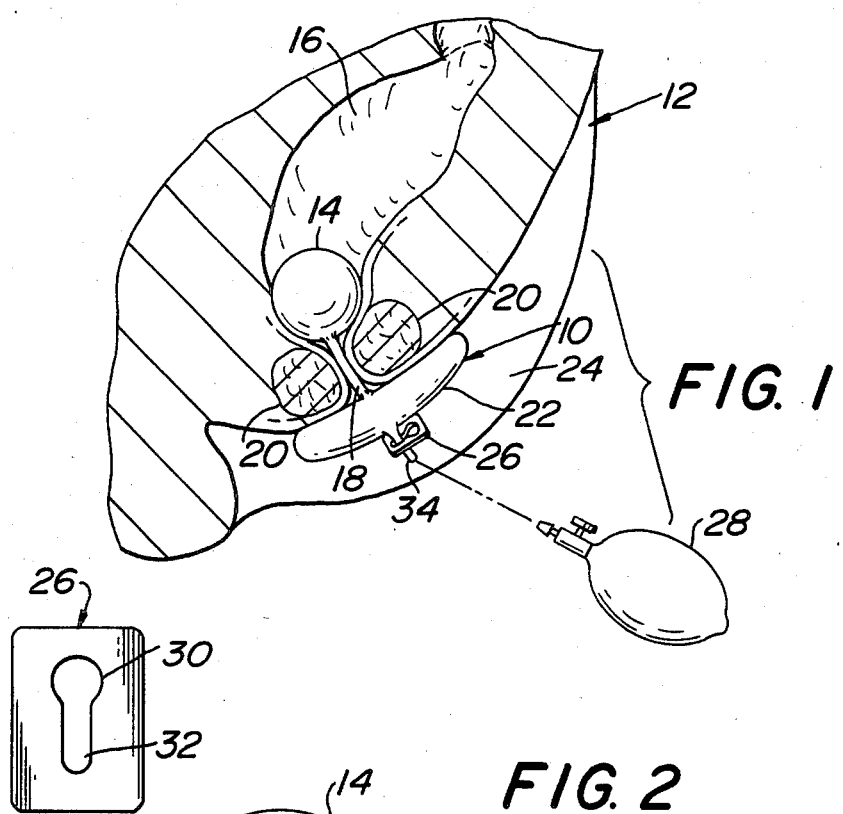
FIG. 1 is a cross-sectional view of an apparatus in accordance with the present invention inserted into the rectum of a male human being for the purpose of controlling fecal incontinence.
Figures 2, 12:
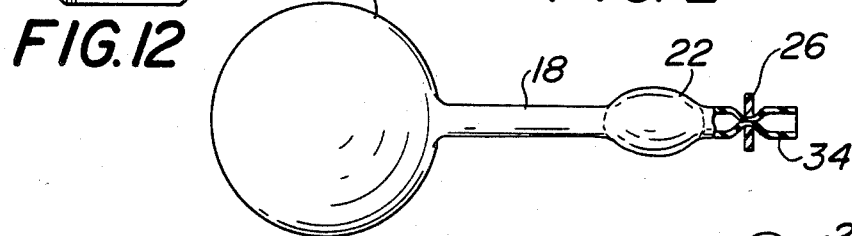
FIG. 2 is a side elevation view of the apparatus of FIG. 1, inflated, but not within the patient.
FIG. 12 is an elevation view of a clip 26 as utilized in FIG. 1.

Referring now to drawings wherein like numerals indicate like elements, there is shown in FIG. 1 an anal obturator 10 inserted in the anus of a patient 12. Obturator 10 is comprised of an inflatable element comprised of three chambers including a first chamber 14 of substantially spherical shape positioned within the rectum 16; a second chamber 18 of a substantially elongated shape which is positioned within the anal sphincter muscles 20 and a third chamber 22 comprising a transverse elongated shaped chamber lying outside of the body between the buttocks 24. A valve means 26 is provided for retaining or releasing the inflating fluid in the chambers. The inflating fluid is preferably air, although any other suitable fluid may be utilized as the inflating medium.

As shown in FIG. 1 the inflatable device 10 may be inflated by an inflation bulb, such as a sphygmomanometer bulb 28. A sphygmomanometer bulb or other special inflation bulb may be provided with obturators when sold, or standard sphygmomanometer bulbs which are typically available on all hospital and nursing home floors may be utilized.

Figures 3, 4:
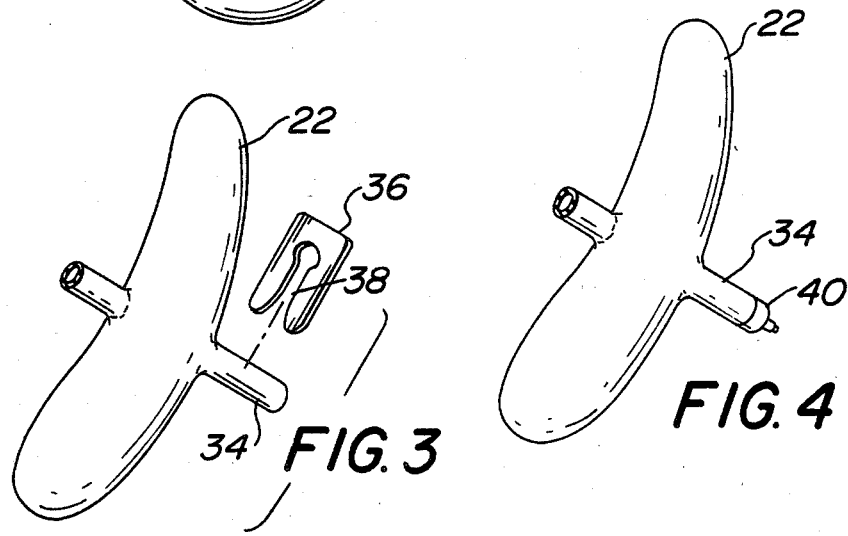
FIG. 3 is a broken away view of the external chamber and a pinch-off valve.
FIG. 4 is a broken away view similar to that of FIG. 3 showing an alternate valve means.

Any suitable valve means may be utilized for selectively retaining or releasing the inflating fluid, such as the compresion clip 26 illustrated in FIG. 1. Compression clip 26 may have an opening having an enlarged portion 30 and a narrow portion 32. The clip 26 would be placed over inflation stem 34 by the use of the enlarged opening 30, with inflation stem 34 being closed or sealed by means of forcing inflation stem 34 into the narrow opening 32. An alternate valve means is shown in FIG. 3 with the use of clip 36, which has a narrow opening 38. Clip 36 may be forced over inflation stem 34, with the narrow opening 38 causing a sealing of inflation stem 34.

Alternatively, as shown in FIG. 4, the inflation stem 34 may be provided with a Schraeder valve, i.e. an inflation valve as commonly used in pneumatic tire stems of automobiles, or other suitable valve 40.

The anal obturator 10 may be made of rubber or other suitable inflatable materials, such as latex. Preferably, the entire inflatable anal occluder 10 is made of formed rubber having a thickeness and consistency approximately equal to that of a conventional rubber ballon.

Referring to FIG. 5 there is shown a blunt trochar 42 provided with a handle 44 and a blunt or round ended shaft 46. The obturator is shown in cross-section substantially deflated, and is marked in FIG. 5 as element 48. The inflated outline is shown in dotted lines at 50.

In operation, the anal obturator of the present invention may be readily utilized to control fecal incontinence in patients in nursing homes, in hospitals, in their homes or anywhere as needed. The inflatable anal obturators could be manufactured efficiently and inexpensively in a manner similar to the manufacture of conventional children's balloons. In this manner, it is presently contemplated and preferred that the anal obturator could be provided as a disposable item, although it is understood that such item could be cleaned and reused.

In use, the anal obturator element 48 is slid over the shaft 46 of trochar 42. The blunt trochar 42 with obturator element 48 thereon is inserted into the anus of the fecally incontinent person. Once inserted, the trochar 42 is removed, the anal obturator 48 is inflated by means of an inflation bulb 28 and then sealed by one of the valve means 26, 36 or 40. If a valve such as a Schraeder valve 40 is utilized, then the inflation bulb would have to have a suitable adapter for connecting to the Schraedr valve.

When it is time to empty the rectum of the person, probably on a daily basis, the valve means is opened, such as by removing the valve clip 26 or 36, which causes a deflation of the anal obturator. Once the anal obturator is deflated, it is readily removed from the rectum and the anus by pulling gently on it. The removal of the anal obturator in itself would tend to stimulate a defecation reflex, causing excretion of the feces. After the feces are excreted, a new or cleaned anal obturator could be inserted in the manner as previously described.

Referring now to FIG. 6 and 7 there is shown another embodiment of the present invention. FIG. 6 shows this embodiment of the present invention as partially inflated, whereas FIG. 7 shows this embodiment in the present invention fully inflated. This particular embodiment may be more useful in connection with the treatment of hemorrhoids in which there is a desire to apply a certain predetermined, but relatively small magnitude of pressure to the inside walls of the anus to compress the hemorrhoidal plexus of veins.

As may be seen in FIGS. 6 and 7, there is comprised a first chamber 52, which is adapted to be positioned within the rectum. The second chamber 54 would be positioned within the anus within the sphincter muscle area. The third chamber 56 is adapted to be positioned external of the body between the buttocks. As may be seen from FIG. 7, the expansion of chamber 54 provides a modicum of expansion and pressure on the internal surface of the anal walls.

An important aspect of the embodiment shown in FIGS. 6 and 7 is the automatic valve 58, which as shown in FIG. 6 which is still open, but in the process of closing. Automatic valve 58 is comprised of a convoluted entrance structure such that when the pressure in chamber 52 reaches a predetermined value, it causes a pinching off of the entrance. This automatic valve 58 is shown in FIG. 7 to be completely closed. In other words, as shown at 60, the pressure within chamber 52 causes pressure on the valve 58 to cause closing at 60 of the passageway for the inflation of chamber 52. Therefore, this embodiment provides an automatic closing off or pinching off of the inflation passageway thereby preventing chamber 52 from inflating beyond a predetermined maximum. In other words, when chamber 52 becomes sufficiently inflated, the valve arrangement 58 automatically closes off the inflation passageway 60 in response to the inflation pressure in chamber 52, preventing further inflation of chamber 52. Further influx of inflation fluid through stem 57 increases the pressure in chambers 54 and 56 causing them, but not chamber 52, to expand. Middle chamber 54 would be the one which would be utilized for dilation. Although pressure would increase in the outer chamber 56, this would not have any significant effect, since chamber 56 is outside of the body cavity.

Additionaly, the structure shown in FIG. 6 may be utilized as an anal obturator where the second portion 54 is comprised of a relatively rigid material such that upon inflation through stem 57, chamber 54 does not expand. The distal end of chamber 54 at automatic valve 58 would be comprised of flexible material so that upon expansion of chamber 52, valve 58 would automatically close upon chamber 52 reaching a predetermined degree of inflation. In this manner, chamber 52 would automatically limit its inflation to a predetermined amount. This would have the desirable effect of automatically providing a maximum diameter for chamber 52 whereit is used as an anal obturator. Upon further inflation, chamber 54 would not expand, but chamber 56 would continue to expand. However, chamber 56 and its degree of expansion would be readily visible to the nurse or other person inflating the anal obturator. In this manner, an anal obturator as shown in FIG. 6, with a chamber 54 having rigid sidewalls, except for the area of automatic valve 58, could be readily inserted by use of a trochar 42. Chamber 54 need not have completely rigid side walls, but only side walls relatively more rigid than the walls of chambers 52 and 56, so that stem area or chamber 54 does not inflate when chambers 52 and 56 are inflated. The nurse or other attendant could rapidly inflate the device, knowing that chamber 52 has an automatic valve 58 which will limit the degree of inflation and the diameter of chamber 52. The nurse would merely need to observe the degree of inflation of chamber 56, and when it has been inflated to the desired degree, could place a clip or valve means 26 or 36 on stem 57 to seal it.

Referring now to FIGS. 8 through 11, there is shown another embodiment of the present invention wherein each of the three chambers is provided with its own separate inflation/deflation passageway. Referring to FIG. 8 there is shown a first chamber 62, a second chamber 64 and a third chamber 66. The first chamber 62 is adapted to be positioned within the rectum, and is inflated by means of passageway 68. Second chamber or middle chamber 64 is adapted to be positioned within the sphincter muscles and is provided with its own separate passageway 70 for the purposes of inflation and deflation. Throughout, where reference is made to the second or middle chamber being positioned "within the sphincter muscles" it is understood that this means that it is positioned within the anus which is surrounded by the internal and external sphincter muscles, and not within the actual body of the muscles themselves. This is also clearly seen in FIG. 1. Third chamber 66 is adapted to be positioned outside of the body between the buttocks and is provided with its own passageway. The three chambers may be positioned on an annular structure or tube 74, and in a preferred embodiment, the passageways 68, 70 and 72 may be formed within the wall of annular structure 74.

In a manner as described with respect to the obturator, particularly with respect to FIG. 5, the dilator structure of FIG. 8 may be inserted into the rectum by means of a blunt trochar, identical to trochar 42. The trochar shaft 46 would be inserted into the central opening 76 of annular structure 74. The passageways 68, 70 and 72 may be provided with tubing extending from the annular structure 74 as shown, and each of the passageway tubings 68, 70 and 72 may be provided with separate valve clips 78, 80 and 82 respectively. Therefore, each of the chambers 62, 64 and 66 may be separately inflated and deflated to any desired degree, independent of any other chamber. The sphygmomanometer bulb may be separately to each of the passageway tubings 68, 70 or 72, and each chamber may be individually sealed when appropriately inflated.

Valve means 78 is shown to be different from valve clips 26 and 36. Valve means 78 may be a threaded valve means which is screwed or turned down on threads to compress the passageway tube 68 to ensure closure. In certain applications, a threaded valve of this type may be desired to preclude the possibility of the valve means being accidently disloged. However, the valve clips are less expensive and may be disposable. Furthermore, the valve clips may be more comfortable for the patient. However, it is understood that valve means, such as valve means 78, may be utilized throughout for the various valve applications disclosed herein.

The anal dilator structure shown in FIG. 8 is particularly adapted for dilation, since the first chamber 62, which is positioned in the rectum, may be inflated to the desired degree and its valve 78 closed. In a similar manner a third chamber 66, positioned outside of the body between the buttocks may be inflated to the desired degree with the inflatable device 61 in the rectum. The dilation performed by second chamber 64, postioned within the anus, surrounded by the anal sphincter muscles, is independent of any effects on inflating chamber 62 in the rectum or chamber 66 between the buttocks.

The anal dilators shown in FIGS. 6, 7, and 8 may be made of rubber or other suitable elastic material as previously described with respect to FIGS. 1 through 5. A trochar substantially identical to trochar 42 with a blunt end may be utilized for insertion of the anal dilators shown in FIGS. 6, 7 and 8. Trochar 42 may be made of any suitable rigid material including hard rubber, plastic, wood or metal. Alternatively, the use of the trochar for insertion may be made unnecessary by making the tubular annular structure sufficiently rigid to enable insertion. Annular structure 74 need not be completely rigid, but only sufficiently rigid to enable it to be inserted, which would still allow it to be somewhat flexible, particularly since lubricating jelly would preferably and commonly be used at the time of insertion.

Referring now to FIGS. 13 and 14, there is shown another embodiment of the present invention wherein the use of an insertion trochar is unnecessary. The apparatus is provided with a tubular stem comprised of a sufficiently rigid, although still flexible, tubular member which enables insertion into the anus of a person without the use of a trochar. If desired or necessary, a slight amount of lubricant may be provided to enhance the ease of insertion, as is commonly used even in rectal examinations.

Preferably, in this embodiment, the apparatus is formed of a material, such as latex or the like, of two different thicknesses. The cross section of the stem is of a thickness substantially greater than the inflatable chambers or portion. The inflatable chambers are formed contiguously with the tubular stem, although they are of a substantially lesser cross sectional thickness to enable ease of inflation while the tubular stem is of sufficient thickness to provide sufficient rigidity to allow insertion without the use of the trochar. The inflatable chamber or portion which is to be inflated in the rectal vault is of a substantially thinner cross section and this portion may collapse over the stem during the process of insertion into the anus. Once inserted into the anus, the terminal balloon portion is inflated to form a ballooned portion within the rectal vault. As described with respect to the other embodiments, a second inflatable chamber is formed along the length of the stem to provide a substantially elongated bananashaped structure transverse to the longitudinal axis of the stem which is adapted, when inflated, to be outside of the body between the buttocks, to provide means for retaining the apparatus in place and to prevent the possibility of the obturator apparatus being drawn or accidentally pushed completely into the anus. Any one of the number of valve apparatus previously described may be utilized for retaining or releasing the inflating fluid within the obturator apparatus of this embodiment.

Referring now to FIGS. 13 and 14 in detail, there is shown an embodiment of the present invention 110 wherein the anal obturator may be inserted without the use of a trochar. FIG. 13 shows this embodiment of the invention in the deflated condition and FIG. 14 shows this embodiment in an at least a partially inflated condition. Referring to FIGS. 13 and 14 together, the apparatus of this embodiment comprises a stem 112 having a stem wall which is of a substantially thicker cross section than the chamber walls of inflatable portions or chambers 114 and 116 to provide the stem 112 with sufficient rigidity to allow insertion into the anus without the use of a trochar. As is conventional in connection with the insertion of devices into orifices of the body, lubrication may be provided with conventionally available lubrication jellies.

As shown in FIG. 13, the apparatus in its deflated condition is readily insertable in the anus with the inflatable portion 14 draped over the relatively rigid stem 112. Once inserted into the anus, inflatable elements 114 and 116 may be inflated as shown in FIG. 14 by the sphygmomanometer bulb 28 of FIG. 1 or other suitable inflation means by connection to opening 118 of stem 112. Once inflated to the desired degree, the stem 112 may be sealed by valve means similar to those described previously, particularly in FIGS. 3, 8 and 12 and by the valve apparatus such as shown in FIGS. 15 and 16. As may be seen in FIG. 14, the cross-sectional dimension of the wall of stem 114 as shown at 120 is substantially greater than the cross-sectional dimension of the chamber wall of inflatable element or chamber 114 as shown at 122. However, the stem 112 may be made sufficiently flexible to allow the use of clamping means as shown at 124 by devices such as those illustrated in FIGS. 15 and 16. Alternatively, a Schraeder valve similar to Schraeder valve 40 may be provided for opening 118. However, preferably, stem 112 is provided with sufficient rigidity to enable insertion with the use of lubrication, but still remains sufficiently flexible to preclude any possibility of discomfort or injury upon insertion.

As described previously, a substantially bananashaped or elongated inflatable chamber 116 is provided to insure proper retention of the apparatus by elongated chamber 116 lying between the buttocks of the person in whom the anal obturator is inserted. In other words, with inflatable chamber 114 in the rectal vault and inflatable chamber 116 inflated between the buttocks, the portion of stem 112 lying between inflated chambers 114 and 116 is positioned in the anal orifice and surrounded by the anal sphincter muscle.

FIG. 15 illustrates a valve clamp 126 which may be provided over stem 112 to cause a clamping action as shown at 124 in FIG. 14 in a manner similar to clip 36 in FIG. 3.

FIG. 16 illustrates a clamping means similar to those shown in FIG. 8 wherein stem 112 may be clamped by applying U-shaped member 128 over the end of stem 112 and turning the knurled disk 130 causing threaded cylinder 132 to be advanced into the U-shaped member 128 causing a positive locked valve mechanism for stem 112. The knurled disk 130 may be provided with a rim 134 which rides in a groove 136 in the U-shaped member 128. U-shaped member 128 may be provided with spring action or resiliency in the side arms wherein the side arms of the U-shaped member 128 may be compressed slightly to allow placing of disk member 130 onto U-shaped member 128.

The apparatus shown in FIGS. 13 and 14 may be molded or otherwise fabricated to provide different thickness of latex or other suitable materials in the stem and in the inflatable portions. The technology of molding unitary devices having different thicknesses of latex in different locations is known in the art. For example, such technology is currently utilized in the fabrication of male catheters known as Texas Catheters. Alternatively, the stem and the inflatable portions may be formed of differing compostions to provide relatively more rigidity in the stem portion.

It will be apparent to those skilled in the art that various modifications may be made to the structures disclosed herein. For example, the self-sealing valve 58 may be utilized at the ends of other chambers. Other types of valve structures may be utilized, other than those disclosed herein. Other shapes of chambers, for example, elliptical rather than spherical, may be utilized. Various compositions may be selected to carry out the functions disclosed. These and other variations will be apparent to those skilled in the art.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. Apparatus for partial insertion into the anus, comprising:
   an inflatable element which comprises a tubular shape having a proximal end and a closed distal end and a plurality of chambers when inflated;
   said plurality of chambers comprising when said element is inserted into the anus and inflated a first chamber extending proximally from the closed distal end of substantially spherical shape adapted to be positioned within the rectum, a second chamber of a substantially elongated shape which is adapted to be positioned within the orifice of the anal sphincter muscles, and a third chamber comprising a transverse elongated shaped chamber adapted when inflated to lie outside of the body between the buttocks:
   said first chamber including a convoluted entrance such that inflation of said first chamber to a predetermined degree causes a closing off of said convoluted entrance.
   an inflation stem at said proximal end of said inflatable element for inflating said chambers; and
   valve means to said inflation stem for retaining or releasing the inflating fluid in said device.

2. Apparatus in accordance with claim 1 wherein said second chamber is provided with a chamber wall comprised of a rigid material along its length and a flexible material at said convoluted entrance to said first chamber.

3. Apparatus in accordance with claim 1 wherein said second chamber is provided with a chamber wall of a flexible and expandable material along its entire length.

* * * * *